Nov. 17, 1970 J. V. PANCHO Plant Pat. 3,004
BOUGAINVILLEA PLANT
Filed Oct. 4, 1968
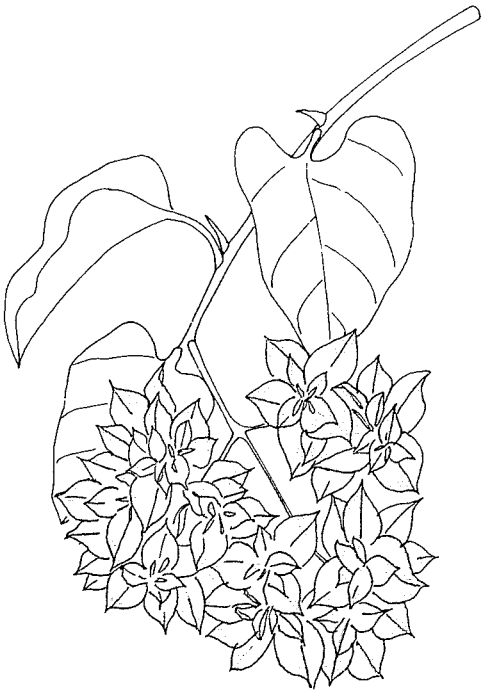
Inventor.
Juan V. Pancho
By: Robb & Robb
Attorneys.

United States Patent Office

Plant Pat. 3,004
Patented Nov. 17, 1970

3,004
BOUGAINVILLEA PLANT

Juan V. Pancho, Laguna, Philippines, assignor of one-half to David Barry, Jr., trading as California Jungle Gardens, Los Angeles, Calif.

Filed Oct. 4, 1968, Ser. No. 765,272
Int. Cl. A01h *5/12*
U.S. Cl. Plt.—54 1 Claim The present invention relates to a new and distinct variety of bougainvillea plant which has discovered by me as a sport in my cultivated garden located at College, Laguna, Philippines.

At the time of my discovery aforesaid, I was growing in my garden plants of the bougainvillea variety known as "Los Banos Beauty" (unpatented) which originated as a sport of the variety known as "Pink Beauty" (unpatented). In the course of growing and caring for my plants of "Los Banos Beauty," I severely pruned the same, and as the plants continued to grow, my attention was attracted to one particular plant among the regular plantings which appeared to be quite different from all the other plants of "Los Banos Beauty." On close inspection of this particular plant, I found that it had sported, and I thereupon carefully preserved the sport, kept it under close observation, and in due course, I asexually reproduced the same by cuttings taken from the sport and grown by me in my garden aforementioned. Continued observations of the spot and the progeny thereof derived from the cuttings aforesaid, have convinced me that it comes true and is established through succeeding propagations, and is a new variety which is distinguished from its parent, as well as from all other bougainvillea varieties of which I am aware, as evidenced by the following unique combination of characteristics which are outstanding therein:

(1) Multiple bracts borne in sets of three upon three upon three, ranging up to 36 bracts, with each set of bracts arising in lieu of flowers where a flower would normally be produced and diminishing in size through each tripling from about 1½ inches in diameter to about 1/16 inch in diameter, giving the bract cluster a tufted appearance from a distance like clustered roses; and (2) A distinctive and attractive white bract color which is suffused with Mallow Purple (Ridgway) from the tip of each bract over about ⅓ of the bract length and along the margins thereof, as depicted in the accompanying drawing.

Except for the white bract color suffused with Mallow Purple as described in the foregoing, as distinguished from the normal solid light pink bract color of the parent variety "Los Banos Beauty," my new variety generally corresponds to the parent variety and accordingly need not be further described in detail. The combined bract multiplicity and white bract color suffused with Mallow Purple, as in my new variety, is unique in the genus Bougainvillea.

I claim:

1. A new and distinct variety of bougainvillea plant, substantially as herein shown and described, characterized particularly as to novelty by the unique combination of multiple bracts borne in sets of three upon three upon three, ranging up to 36 bracts, with each set of bracts arising in lieu of flowers where a flower would normally be produced and diminishing in size throughout each tripling from about 1½ inches in diameter to about 1/16 inch in diameter, giving the bract cluster a tufted appearance and appearing from a distance like clustered roses, and a distinctive and attractive white bract color which is suffused with Mallow Purple (Ridgway) from the tip of each bract over about ⅓ of the bract length and along the margins thereof, as depicted in the accompanying drawing.

No references cited.

ROBERT E. BAGWILL, Primary Examiner